United States Patent
Vahala

(10) Patent No.: US 10,376,716 B2
(45) Date of Patent: Aug. 13, 2019

(54) RADIATION THERAPY SYSTEM WITH REAL-TIME MAGNETIC RESONANCE MONITORING

(71) Applicant: KONINKLIJKE PHILIPS N.V., Eindhoven (NL)

(72) Inventor: Erkki Tapani Vahala, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/784,635

(22) PCT Filed: Apr. 18, 2014

(86) PCT No.: PCT/EP2014/058009
§ 371 (c)(1),
(2) Date: Oct. 15, 2015

(87) PCT Pub. No.: WO2014/170483
PCT Pub. Date: Oct. 23, 2014

(65) Prior Publication Data
US 2016/0082288 A1    Mar. 24, 2016

(30) Foreign Application Priority Data
Apr. 18, 2013   (EP) .................................... 13164297

(51) Int. Cl.
A61B 5/055   (2006.01)
A61B 5/00    (2006.01)
(Continued)

(52) U.S. Cl.
CPC ............ *A61N 5/1039* (2013.01); *A61B 5/055* (2013.01); *A61B 5/4836* (2013.01); *A61B 5/7271* (2013.01); *A61B 5/742* (2013.01); *A61B 5/7405* (2013.01); *A61N 5/1037* (2013.01); *A61N 5/1075* (2013.01); *G01R 33/4808* (2013.01);
(Continued)

(58) Field of Classification Search
CPC ..... G01R 33/20; G01R 33/44; G01R 33/4808
See application file for complete search history.

(56) References Cited

U.S. PATENT DOCUMENTS

| 7,741,624 B1 | 6/2010 | Sahadevan |
| 2007/0076846 A1* | 4/2007 | Ruchala ................. A61N 5/103 378/65 |

(Continued)

FOREIGN PATENT DOCUMENTS

| CN | 101961530 A | 2/2011 |
| WO | 2009156896 A1 | 12/2009 |
| WO | 2011127946 A1 | 10/2011 |

OTHER PUBLICATIONS

"Real-Time Adaptive Methods for Treatment of Mobile Organs by MRI-controlled High-Intensity Focused Ultrasound" by B.D. Senneville et al. Magnetic Resonance in Medicine 57:319-330 (2007).*

*Primary Examiner* — Baisakhi Roy
*Assistant Examiner* — Jason M Ip
(74) *Attorney, Agent, or Firm* — Sherry Womack Austin

(57) ABSTRACT

Prior to the radiotherapy, an MR guided radiotherapy device acquires MR data and tracks structures relevant to the radiotherapy treatment. These MR data are displayed to a user. Furthermore, these data are used to calculate a quality factor for the treatment.

19 Claims, 2 Drawing Sheets

(51) Int. Cl.
*G01R 33/48* (2006.01)
*A61N 5/10* (2006.01)

(52) U.S. Cl.
CPC .............. *A61N 2005/1034* (2013.01); *A61N 2005/1054* (2013.01); *A61N 2005/1055* (2013.01); *A61N 2005/1074* (2013.01)

(56) References Cited

U.S. PATENT DOCUMENTS

| | | | |
|---|---|---|---|
| 2008/0049897 A1* | 2/2008 | Molloy | A61N 5/1042 378/65 |
| 2008/0159478 A1 | 7/2008 | Keall | |
| 2008/0212737 A1* | 9/2008 | D'Souza | A61N 5/1049 378/65 |
| 2010/0056908 A1 | 3/2010 | Giller et al. | |
| 2011/0199083 A1 | 8/2011 | Nauerth | |
| 2011/0201920 A1* | 8/2011 | Allen | A61N 5/1042 600/411 |
| 2012/0069962 A1 | 3/2012 | Fallone et al. | |
| 2013/0035588 A1 | 2/2013 | Shea | |
| 2013/0193352 A1 | 8/2013 | Bert | |
| 2013/0274539 A1 | 10/2013 | Yamada et al. | |

* cited by examiner

RADIATION THERAPY SYSTEM WITH REAL-TIME MAGNETIC RESONANCE MONITORING

CROSS REFERENCE TO RELATED APPLICATIONS

This application is a U.S. national phase application of International Application No. PCT/EP2014/058009, filed on Apr. 18, 2014, which claims the benefit of EP Application Serial No. 13164297.7 filed on Apr. 18, 2013 and is incorporated herein by reference.

FIELD OF THE INVENTION

The invention relates to a device in the field of MR guided radiotherapy and more specifically to the magnetic resonance monitoring of structure motion.

BACKGROUND OF THE INVENTION

A radiotherapy system with real-time magnetic resonance monitoring is known from WO2009/156896 A1. The described system allows for real-time monitoring for radiation.

The described system compares real-time monitoring images with a reference image during radiotherapy by using an image comparator to identify any changes in the subject since the radiotherapy planning stage. This information may be used for repositioning of the subject or for updating the radiotherapy plan. The updated radiotherapy plan adjusts the subsequently applied radiation pulses to adapt the radiotherapy plan to accommodate the identified subject motion.

US2013035588 describes methods, systems and computer readable media for therapy planning using magnetic resonance imaging. The motion or position of the treatment region is tracked over time for many cycles using MRI. The tracking is used to compare with the surrogate motion or signal to establish the long term surrogate-to-tumor correspondence. The motion of the object is compared to the surrogate motion (determined by measurements of the motion or position of tissue (e.g. skin or chest) or using navigation images). The comparison is used to determine whether the position variation of the object in the cycle results in inaccuracies in the gated treatment. Furthermore, US2013035588 describes that a determined position is used for therapy planning. The position is used for planning using tumoral spatial probability density functions.

SUMMARY OF THE INVENTION

It is an object of the invention to improve quality assurance for magnetic resonance guided radiotherapy In general, prior to (MR-guided) radiotherapy, MR or CT scans are made from a subject. Scans made during this stage are here called planning scans and the phase during which planning scans are acquired is here called the planning phase. Based on these planning scans, the important structures for treatment are delineated. A structure could for example be (a part of) a subject to be treated, a tumor, but also a (healthy) organ at risk, which needs to be spared. These delineations are used to calculate a radiotherapy plan. By calculating a radiotherapy plan, the radiation dose to the subject is optimized in such a way that the radiation dose to the tumor is sufficiently high, while keeping the planned radiation dose to the organs at risk within safety limits. A radiotherapy plan could for example describe linear accelerator or multileaf collimator positions and dose to be delivered on certain linear accelerator/multileaf collimator positions.

However, periodic, irregular, and shape-changing structure motion during radiotherapy, e.g. due to respiration, shaking, or swelling of an organ hampers the effectiveness of the radiotherapy and introduces unwanted irradiation. The combination of a magnetic resonance examination system with a radiotherapy system allows the real-time monitoring of (soft) tissue during treatment. During real-time monitoring, MR data, such as images or navigators, are acquired from the structure with a data rate frequency, which is larger than the frequency of dynamic process causing the structure motion. These processes could for example be breathing related motion (0.2-1 Hz) or heartbeat (~1 Hz). Structure motion can for example be compensated for by means of gating or (online) changes in the radiotherapy treatment: e.g. movement of the subject bed in the MR radiotherapy system, motion of the radiotherapy system, change in multi-leaf collimator positions to follow small movements, and recalculation of a radiotherapy plan. However, all these compensation methods have limitations in their capabilities to compensate for structure motion. This may result in unnecessary toxicity, treatment delay or undertreatment of a tumor. Therefore proper quality assurance prior to radiotherapy is important.

An insight of the invention is that knowledge prior to the actual radiotherapy on the (variation) in structure motion is of importance for the quality assurance of the treatment. Prior to treatment, during the here called quality assurance phase, the magnetic resonance examination system acquires scans from a subject on an imaging table. These scans are here called quality assurance scans. Based on these quality assurance scans, one or more structures are identified, for example by semi-automatic segmentation. The structures are automatically tracked by structure tracking software. Structure tracking during the quality assurance and planning phase can be real-time. Real-time tracking is advantageous for efficiency reasons. However, this is not required for the achieve the object of the invention. For example, for the purpose of gating it is enough that structure motion is still within a similar range as during the planning phase. To this end structure tracking does not need to be real-time and can also be done after all magnetic resonance images have been required. Structure motion information may be displayed to a user, who can use it for quality assurance.

The structure motion information and/or quality of structure tracking during the quality assurance phase serve as a representative for the structure motion information and/or quality of structure tracking during radiotherapy. This puts restrictions on the time between quality assurance phase and the radiotherapy. Preferably, the quality assurance scans are acquired during a time slot in which the subject is already on a treatment table.

According to one aspect of the invention, an additional quality assurance phase is performed prior to the quality assurance phase. The additional quality assurance phase will be further called "initial quality assurance phase". The initial quality assurance phase may be combined with the planning phase in order to use structure motion information and/or quality of structure tracking to optimize the radiotherapy plan. Structure motion information and/or information about the structure tracking quality retrieved during the initial quality assurance phase may be compared to structure motion information and/or information about the structure tracking quality retrieved during the quality assurance phase, e.g. in order to investigate if assumptions used during the creation of the radiotherapy plan are still valid.

Structure motion information can be the structure motion itself, but also a statistical measure determined by the structure motion (e.g. a standard deviation or variance of cyclic structure motion, minimum, mean or maximum amplitude of structure motion, mean structure position, confidence interval for structure position). As structure motion may result in undertreatment or overtreatment of certain structures, structure motion information may for example help in a decision to deliver radiotherapy as planned, not to deliver radiotherapy or to adapt the radiotherapy plan to better fit the (variation) in structure motion and changes herein since the initial quality assurance phase. A decision to adapt the radiotherapy plan or a decision not to deliver the radiotherapy plan may for example be a result of expected software and/or hardware problems in tracking and/or following the structure motion. A radiotherapy plan can be safely delivered if expected undertreatment or overtreatment of a structure is within a clinically acceptable range.

Results of the structure tracking software may be displayed to a user. For example, the trajectory itself may be displayed to the user. This could for example be done by means of a centre of mass line, a cine display, where the user can scroll over the respiratory cycle. The organ position can be shown as an intersection line on the current slice; or; as a filled, (semi)opaque intersection; or as a shaded (semi) opaque 3D object; or as a shaded semi-opaque 3D object with an intersection line. Also, reconstructed magnetic resonance data (e.g. images, navigators) in combination with tracking results may be displayed to the user.

In some of the embodiments, motion analysis software is coupled to the structure tracking software for calculating a quality factor based on the structure motion information and one or more pre-set limits for the structure motion information. In some embodiments the quality factor is displayed to the user to facilitate in the quality assurance process.

According to one embodiment of the invention, the quality factor is calculated based on a comparison between structure motion information from the initial quality assurance phase and structure motion information from the quality assurance scans. In this way can be ensured that assumptions used when the radiotherapy plan was calculated, are still valid.

According to one embodiment, the variation in the structure motion is quantitatively displayed to the user. This may help to identify sources of variation in motion. This may help in optimizing a motion minimizing technique, e.g. using breath-hold or optimizing the positioning of fixating devices. Also measures describing the variation in the cyclic structure motion can be compared with a pre-set limit for this variation in order to calculate the quality factor.

In one embodiment, the user can provide feedback to the structure tracking software in order to improve tracking accuracy. Furthermore, in another embodiment, the user may request scan data of a different type, e.g. in terms of contrast, resolution or dimension, during phases in the motion cycle that are identified as or expected to be problematic. One could for example use navigators during most of the breathing cycle and switch to a 2D image in the breathing phase in which tracking based on navigators is too complicated. In this way the accuracy of the structure tracking may be improved.

According to another embodiment, the structure tracking software compares the structure motion information with the limitations in the motion compensating hardware and/or software in order to calculate the quality factor.

In another embodiment, the structure motion information retrieved prior to treatment is passed to an optimization routine that performs lengthy optimization routines prior to radiotherapy in order to reduce the real-time calculation requirements of the hardware during radiotherapy.

According to one embodiment, the structure motion information is combined with information on the limitations in motion compensating hardware and/or software, in order to calculate a radiation dose that will be delivered to a structure when these conditions remain unchanged during the actual treatment. The radiotherapy plan and possibly quality measures (for example based on a dose volume histogram) of this radiotherapy plan are provided to the user, who can grant a permission to continue with the radiotherapy if all quality measures are within pre-set limits.

In case the resulting radiotherapy plan does not fulfil the predefined quality measures in one embodiment a new radiotherapy plan is calculated, which incorporates limitations in tracking accuracy.

These and other aspects of the invention will be apparent from and elucidated with reference to the embodiments described hereinafter.

DETAILED DESCRIPTION OF THE INVENTION

Figure 1:
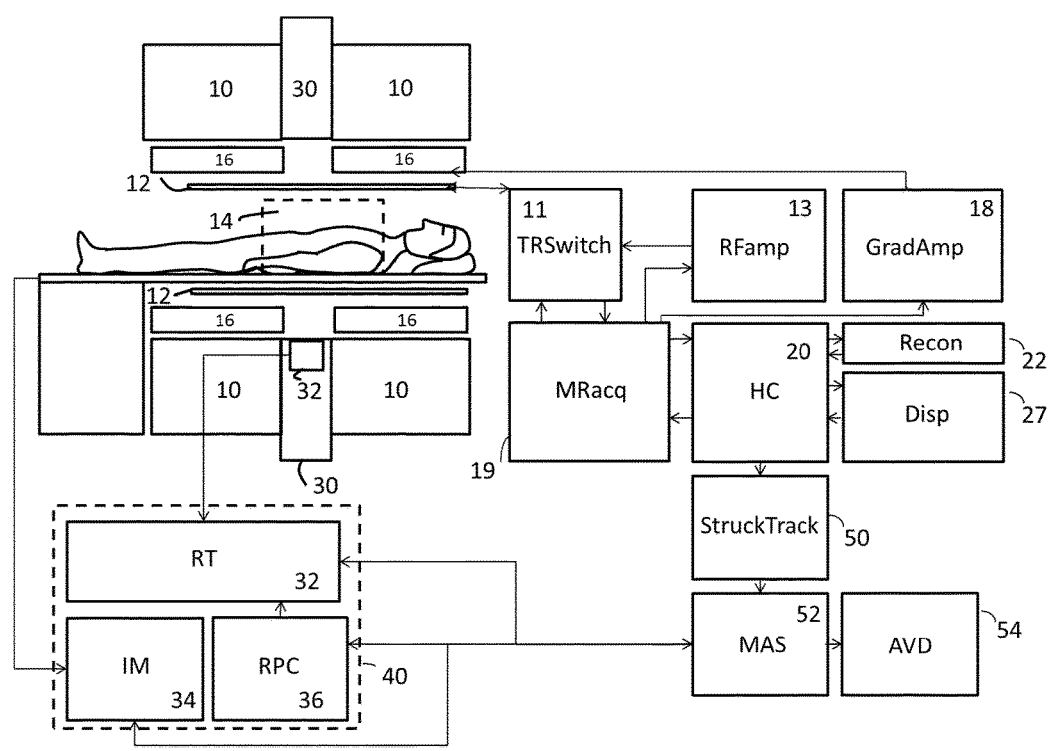
FIG. 1 illustrates diagrammatically a magnetic resonance guided radiotherapy system in which the invention is used.

FIG. 1 illustrates diagrammatically a magnetic resonance guided radiotherapy system in which the invention is used.

The magnetic resonance examination system comprises a main magnet 10 which generates a steady homogeneous main magnetic field within the examination zone 14. This main magnetic field causes a partial orientation of the spins in the patient to be examined along the field lines of the main magnetic field. An RF system 12 is provided with one or more RF antennae to emit an RF excitation electromagnetic field into the examination zone 14 to excite spins in the body of the patient to be examined. The relaxing spins emit magnetic resonance signals in the RF range which are picked up by the RF antennae, notably in the form of RF receiving coils 12. The RF system may be coupled to an Tx/Rx switch (TRSwitch) 11, which in turn is coupled to an RF amplifier (RFamp) 13. Further, gradient coils 16 are provided to generate temporary magnetic gradient fields, notably read gradient pulses and phase encoding gradients. These gradient fields usually are orientated in mutual orthogonal directions and impose spatial encoding on the magnetic resonance signals. Gradient amplifiers 18 (GradAmp) are provided to activate the gradient coils to generate the magnetic gradient encoding fields. The magnetic resonance signals picked up by the RF receiver antennae 12 are applied to an MRI data acquisition system (MRacq) 19. The MRI data acquisition system 19 provides the data to a host computer (HC) 20, which in turn provides it to a reconstructor (Recon) 22, which may reconstruct an image from the data. These data may be displayed on a display (Disp) 27.

The radiotherapy system (RT) 32 includes a housing 30 or other support or body supporting a radiation source arranged to move or revolve around the subject. The radiotherapy system 32 may contain a multi-leaf collimator (MLC). The combination of the multi-leaf collimator with the motion of the radiation source around the subject allows the delivery of complex dose distributions by means of for example arc therapy or intensity modulated radiation therapy. Structure motion can be compensated for by means of motion compensation software and/or hardware 40. Examples of motion compensation that can be performed by means of hardware are movement of an imaging table (IM) 34 or movement of the leaves in the MLC. An example of motion compensation by means of software could be online recalculation or updating of the radiotherapy plan, e.g. by means of choosing from an atlas of precalculated radiotherapy plans, by means of a radiotherapy plan calculator (RPC) 36.

The structure tracking software (StruckTrack) 50 is coupled to the magnetic resonance examination system. Before tracking, the structures of interest need to be segmented. This could be done manually or by (semi-)automatic segmentation. (Semi-) automatic segmentation can for example be performed by atlas-based segmentation, cluster-based segmentation, model-based segmentation, or techniques like livewire. The actual tracking, which may start as soon as the first structure is segmented, can for example be done by means of registration based tracking, navigator based tracking or optical flow tracking. Information about a structure motion is displayed to a user by means of an audio/visual display (AVD) 54 prior to treatment, which could be the display used in the MR system. The structure motion information can be used for quality assurance.

In some of the embodiments, the trajectory itself is displayed to the user. This could for example be done by means of a centre of mass line, a cine display, where the user can scroll over a structure's motion cycle. The organ position can be shown as an intersection line on the current slice; or; as a filled, (semi)opaque intersection; or as a shaded (semi)opaque 3D object; or as a shaded semi-opaque 3D object with an intersection line. Also, reconstructed magnetic resonance data (e.g. images, navigators) in combination with tracking results may be displayed to the user.

In some of the embodiments, structure motion information is provided by the structure tracking software 50 to motion analysis software (MAS) 52. The motion analysis software 52 compares the structure motion information with one or more pre-set limits for the structure motion information and calculates a quality factor for the treatment to be delivered. Structure motion information may be the structure motion itself or a statistical measure determined by the structure motion (e.g. a standard deviation or variance of cyclic structure motion, minimum, mean or maximum amplitude of structure motion, mean structure position, confidence interval for structure position). This statistical measure may also be calculated by the motion analysis software.

The value of the quality factor is determined by a certain characteristic, describing the structure motion, falling within a safety range set by one or more pre-set limits, or not. The quality factor is displayed to a user by means of an audio/visual display 54 and does not need to be a number, but could for example also be a colour. For example the colour red can be used if a characteristic describing the structure motion does not fall within a range set by one or more pre-set limits and the colour green can be used if the characteristic does fall within the range set by one or more pre-set limits.

In one embodiment of the invention, the quality factor is calculated based on a comparison between structure motion information retrieved in the initial quality assurance phase and structure motion information retrieved in the quality assurance phase. For example, during the initial quality assurance phase a 4D CT or MR plan can be created and images are associated with a motion signal from a respiratory device or MR navigator(s). A target position in images can be defined as $f_{plan}(t_n)$, where $t_n$ is a discrete timestamp in a motion cycle. During the quality assurance phase, a new $f_{treat}(t_n)$ is measured. The quality factor can be calculated for example by comparing measures like a root mean square of the difference between $f_{plan}(t_n)$ and $f_{treat}(t_n)$ or a simple $\max(\mathrm{abs}(f_{plan}), \mathrm{abs}(f_{treat}))$, with one or more pre-set limits for these measures.

In another embodiment $f_{treat}(t_n)$ can also be examined over several breathing cycles to calculate inter-cycle variations. For example, the variation in the structure's centre of mass and/or edge positions over time can be displayed to a user in a quantitative way. This could for example be done by displaying error bars on the structure positions in the cine display or by varying the line thickness representing the structure position over time. The size of the error bar or the line thickness can be related to a statistical measure representing the variation in the movement. Examples of these statistical measures could be the standard deviation, the 95% confidence interval or the maximum variation. In another embodiment, the quality factor is calculated based on these statistical measures and one or more pre-set limits for these statistical measures.

In one embodiment, the user can highlight potential tracking problems in a structure's motion and provide the system with feedback on the structure's position and shape. This information is used by the system to redefine the characteristics/textures/model used to segment a structure during tracking.

In another embodiment the user can request the software to acquire images of a different scan type, for example, in terms of resolution, dimensions or contrast, at the phase(s) in the cycle where tracking problems are expected or identified. One could for example use navigators during most of a breathing cycle and switch to a 2D image in more difficult parts of the breathing cycle by means of scan interleaving.

In another embodiment, one or more pre-set limits are determined by the limitations of the motion compensating software and/or hardware 40. These limitations are, for example, a delay in the control circuit that controls the compensating movement of the imaging table, the radiotherapy system and the multi-leaf collimator. Another example of such a limitation is the time needed to calculate a new radiotherapy plan or the time needed to identify the best radiotherapy plan from a precalculated atlas of radiotherapy plans.

In another embodiment prior to treatment, the structure motion information is passed to an optimization routine prior to radiotherapy in order to reduce real-time calculation requirements during radiotherapy. This can be done in a similar way as 4D CT treatment planning known as such in the art, for example by calculating atlas look-up tables with organ positions as keys into tables.

In another embodiment, if structure motion speed differs from the initial quality assurance phase, hardware parameters can be recalculated (e.g., multileaf collimator movement commands for predictive positioning of the beam) to optimize the hardware speed settings.

In one embodiment, wherein structure motion information is provided to the radiotherapy plan calculator 36 in order to calculate a dose to a structure in case the radiotherapy plan will be given as planned, given the limitations in the motion compensating software and/or hardware and the structure's motion. A fast method for parallel calculations with GPUs, e.g., monte-carlo, could be used. A simpler smearing of the dose area on the images could also be used, based on the uncertainties in the structure's motion cycle and noise in the tracking signal. In another embodiment the quality factor is calculated based on this radiotherapy plan. For example quality, measures like dose-volume histogram (parameters) or results from a gamma analysis are calculated and compared with one or more pre-set limits for these parameters.

In another embodiment, in the quality assurance phase a new radiotherapy plan is calculated. This could for example be done in the following way. When an original plan is created with monte carlo-based ray simulation, the tissue is formed from non-overlapping, closed shapes and OBB tree is used to divide the world volume into small enough cubes with limited number of vertices of tesselated shapes (to be computationally effective for simulation purposes). During simulation, whenever a ray trespasses a cube or its dose is deposited into the cube, its ID is associated with the cube. When, during the quality assurance phase, a slight organ movement (as compared to the plan) is detected, and the new organ position is not available in (pre-) generated plan atlas, recalculation is triggered. Recalculation removes the effects of the simulated rays that passed through the union of the old and new organ shape cubes. It then re-adds the organ in new position and resimulates removed rays. This results in an updated radiotherapy plan, which may be displayed to the user.

Figure 2:
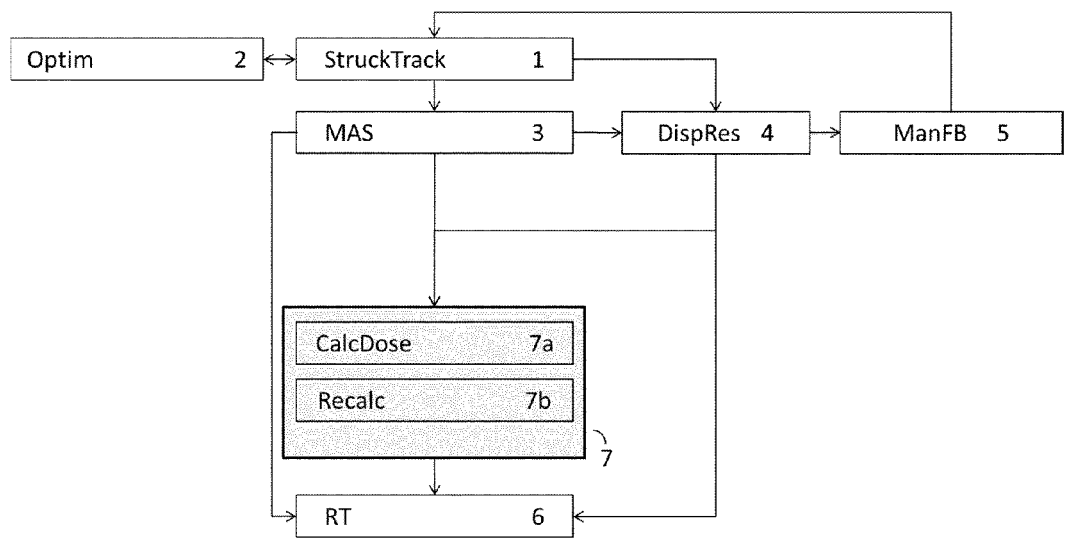
FIG. 2 illustrates a possible workflow of the quality assurance process

FIG. 2 illustrates a possible workflow of the quality assurance process. During the quality assurance process, structure tracking is performed (StruckTrack) 1. Structure tracking results may be passed to the optimization routine to reduce real-time calculation requirements (Optim) 2, or to the motion analysis software in order to calculate a quality factor for the radiotherapy (MAS) 3, or the results may be displayed to the user (DispRes) 4. These displayed results may in turn be used by a user in order to provide feedback (ManFB) 5 to the system to improve the structure tracking. For example, the user can request the software to acquire images of a different scan type. Based on the displayed results, a user may also provide permission to start the radiotherapy (RT) 6.

The permission to start the radiotherapy 6 may also be given based on the quality factor calculated by the motion analysis software 3. Furthermore, the quality factor may be used to calculate a new dose plan (CalcDose) 7a and/or to recalculate parameters for the motion compensating hardware (Recalc) 7b.

Whilst the invention has been illustrated and described in detail in the drawings and foregoing description, such illustrations and description are to be considered illustrative or exemplary and not restrictive; the invention is not limited to the disclosed embodiments and can be used for timing the quality assurance in various applications within the field MR guided therapy.

The invention claimed is:

1. A magnetic resonance guided radiotherapy system comprising:
   a magnetic resonance examination system configured to acquire magnetic resonance signals of a subject within an examination zone before and during radiotherapy, the magnetic resonance signals being indicative of motion of a structure of the subject;
   a radiotherapy system comprising a linear accelerator with a multi-leaf collimator, the radiotherapy system configured to perform the radiotherapy on the subject in accord with a radiotherapy plan identifying linear accelerator and multi-leaf collimator positions, the radiotherapy plan generated prior to performing the radiotherapy and assuming the motion of the structure of the subject within the examination zone indicated by the magnetic resonance signals acquired before radiotherapy;
   one or more computer processors programmed to:
      control the radiotherapy system to perform the radiotherapy according to the radiotherapy plan,
      during performing the radiotherapy, monitoring the motion of the structure of the subject in the examination zone by the magnetic resonance signals acquired of the subject during radiotherapy,
      generate a quality factor comparing (1) a variation between the motion of the structure indicated by the magnetic resonance signals acquired before the radiotherapy and the motion of the structure indicated by the magnetic resonance signals acquired during the radiotherapy with (2) one or more pre-set limits related to the variation, wherein at least one of the one or more pre-set limits is determined based on a limitation of the radiotherapy system to adjust delivery of the radiotherapy during motion of the structure during the radiotherapy, the one or more pre-set limits including a delay in a control circuit that controls compensating movement of an imaging table of the magnetic resonance examination system, the radiotherapy system and the multi-leaf collimator;
      recalculate the radiotherapy plan including recalculating multi-leaf collimator movement commands based on a comparison between the structure motion before radiotherapy with structure motion during delivery of the radiotherapy when the generated quality factor indicates the assumption of the motion of the structure of the subject within the examination zone indicated by the magnetic resonance signals acquired before radiotherapy is not valid; and
      control the radiotherapy system to adjust radiation therapy to a patient according to the recalculated radiotherapy plan.

2. The magnetic resonance guided radiotherapy system as set forth in claim 1, wherein the one or more processors are further configured to monitor and track the structure motion based on the magnetic resonance signals during the radiotherapy.

3. The magnetic resonance guided radiotherapy system as claimed in claim 1 comprising:
   a visual display configured to be controlled by the one or more processors to display the quality factor.

4. The magnetic resonance guided radiotherapy system as set forth in claim 3, wherein the display is further controlled by the one or more processors to display the variation in the structure motion in a quantitative way.

5. The magnetic resonance guided radiotherapy system as set forth in claim 4, wherein the quality factor is displayed as a numbered value.

6. The magnetic resonance guided radiotherapy system as set forth in claim 1, wherein the one or more processors are further configured to calculate an actual radiation dose delivered to the structure of the subject during the radiotherapy.

7. The magnetic resonance guided radiotherapy system as set forth in claim 6, wherein the one or more processors are further configured to calculate the radiation dose which should have been delivered to the structure of the subject.

8. The magnetic resonance guided radiotherapy system as set forth in claim 1 further configured to receive feedback from a user.

9. The magnetic resonance guided radiotherapy system as set forth in claim 1, wherein the structure motion is cyclic motion and wherein the one or more computer processors are further programmed to interleave at least two scan types during one motion cycle.

10. The magnetic resonance guided radiotherapy system as set forth in claim 1 further comprising: an audio-video display configured to output at least one of an audio or video indication of the quality factor.

11. The magnetic resonance guided radiotherapy system as set forth in claim 9, wherein the one or more processors are further configured to:
  generate a diagnostic image from the magnetic resonance signals;
  calculate a trajectory of the structure motion in one cycle of the cyclic motion under the radiation therapy plan;
  during the radiotherapy, calculate a trajectory of the structure motion in a current cycle;
  control a display to display the diagnostic image, the therapy plan trajectory, and the current cycle trajectory and indicate the quality factor by at least one of color and graphics, the quality factor being indicative of quality of delivery of radiotherapy.

12. A magnetic resonance guided radiotherapy system for delivering radiotherapy to a structure of a subject in an examination zone, which structure is undergoing cyclic motion, the system comprising:
  a magnetic resonance system configured to acquire magnetic resonance signals of the structure in the examination zone before and during the delivery of the radiotherapy; and
  one or more computer processors programmed to:
    reconstruct the magnetic resonance signals received before the delivery of radiotherapy into a planning image and reconstruct the magnetic resonance signals received during the radiotherapy into a treatment image,
    using the magnetic resonance system, track a trajectory of a target position $f_{plan}$ in the planning image over a motion cycle before commencing delivery of the radiotherapy,
    generate a radiotherapy plan identifying linear accelerator and multi-leaf collimator positions using the planning image and on the assumption of motion indicated by the trajectory of the target position before commencing delivery of the radiotherapy;
    using the magnetic resonance system, track a trajectory of a target position $f_{treat}$ of the structure in the examination zone after commencing delivery of the radiotherapy,
    determine a difference between the trajectories of the target positions before and during the delivery of the radiotherapy,
    compare the difference with one or more pre-set limitations to define a quality factor, the one or more pre-set limitations including at least a delay in a control circuit that controls compensating movement of an imaging table of the magnetic resonance examination system, the radiotherapy system and the multi-leaf collimator;
    recalculating the new radiotherapy plan if the comparison indicates the assumption of motion indicated by the trajectory of the target position before commencing delivery of the radiation therapy is not valid; and
    control a therapy device comprising a linear accelerator with a multi-leaf collimator, the radiotherapy system to deliver radiotherapy according to the new radiotherapy plan.

13. The magnetic resonance guided radiotherapy system as set forth in claim 12 wherein the quality factor is displayed numerically.

14. The magnetic resonance guided therapy system as set forth in claim 13 wherein the indication of the quality factor is set forth graphically.

15. A magnetic resonance guided radiotherapy system comprising:
  a magnetic resonance examination system configured to acquire magnetic resonance signals of a subject within an examination zone, the magnetic resonance signals being indicative of motion of a structure of the subject;
  a radiotherapy system comprising a linear accelerator with a multi-leaf collimator configured to perform radiotherapy on the subject based on a radiotherapy plan identifying linear accelerator and multi-leaf collimator positions, wherein the radiotherapy plan is based on Monte Carlo-based ray simulation for motion of the structure determined prior to performing the radiotherapy; wherein
    the radiotherapy system is configured to move a radiation source of the linear accelerator about the subject within the examination zone, and
    the magnetic resonance examination system is further configured to acquire the magnetic resonance signals before delivering the radiotherapy to determine if the radiotherapy plan can be safely delivered to the subject given the structure motion;
  wherein the magnetic resonance guided radiotherapy system further comprises one or more computer processors configured to:
    track the motion of the structure based on the magnetic resonance signals acquired before delivering the radiotherapy,
    compare the structure motion tracked before the radiotherapy with the motion of the structure tracked after commencing delivery of the radiotherapy,
    compare a variance between motion of the structure tracked before the delivery of the radiotherapy and the motion of the structure tracked after commencing the radiotherapy with at least one pre-set limit including a delay in a control circuit that controls compensating movement of an imaging table of the magnetic resonance examination system, the radiotherapy system and the multi-leaf collimator
    calculate a new radiotherapy plan based on Monte Carlo-based ray simulation for motion of the structure tracked after commencing the radiotherapy if the comparison of the variance with the at least one pre-set limit indicates detection of organ movement compared with the radiotherapy plan; and
    control a therapy device to deliver radiotherapy according to the new radiotherapy plan.

16. The magnetic resonance guided radiotherapy system as set forth in claim 1, wherein the one or more pre-set limitations further include at least a time needed to calculate a new radiotherapy plan based on the determined difference between the trajectories.

17. The magnetic resonance guided radiotherapy system as set forth in claim 12, wherein the one or more pre-set limitations further include a limitation of the radiotherapy system to adjust delivery of the radiotherapy.

18. The magnetic resonance guided radiotherapy system as set forth in claim 12, wherein the one or more processors are further programmed to deliver radiation therapy to a patient when the generated quality factor is above a threshold.

19. The magnetic resonance guided radiotherapy system as set forth in claim 15, wherein the one or more processors are further programmed to deliver radiation therapy to a patient when the generated quality factor is above a threshold.

* * * * *